(12) United States Patent
Felber (10) Patent No.: US 9,518,575 B2
(45) Date of Patent: Dec. 13, 2016

(54) VACUUM PUMP (71) Applicant: MEDELA HOLDING AG, Baar (CH)

(72) Inventor: Armin Felber, Lucerne (CH)

(73) Assignee: MEDELA HOLDING AG, Baar (CH)

( * ) Notice: Subject to any disclaimer, the term of this patent is extended or adjusted under 35 U.S.C. 154(b) by 327 days.

(21) Appl. No.: 14/348,560

(22) PCT Filed: Sep. 27, 2012

(86) PCT No.: PCT/CH2012/000222
§ 371 (c)(1),
(2) Date: Mar. 28, 2014

(87) PCT Pub. No.: WO2013/049944
PCT Pub. Date: Apr. 11, 2013

(65) Prior Publication Data
US 2014/0227112 A1 Aug. 14, 2014

(30) Foreign Application Priority Data
Oct. 4, 2011 (CH) .................................... 1627/11

(51) Int. Cl.
A61M 1/06 (2006.01)
F04B 43/00 (2006.01)
A61M 1/00 (2006.01)

(52) U.S. Cl.
CPC ........ F04B 43/0081 (2013.01); A61M 1/0066 (2013.01); A61M 1/0072 (2014.02);
(Continued)

(58) Field of Classification Search
CPC ...... A61M 1/06; A61M 1/064; A61M 1/0027; A61M 1/0031; G01L 9/0076
See application file for complete search history.

(56) References Cited

U.S. PATENT DOCUMENTS 7,238,165 B2 * 7/2007 Vincent ............... A61M 1/1053
417/412
2003/0116702 A1 6/2003 Schulz et al.
(Continued)

FOREIGN PATENT DOCUMENTS

JP 2007181735 A 7/2007
WO WO-03/034014 A2 4/2003
(Continued)

OTHER PUBLICATIONS

International Search Report for PCT/CH2012/000222, dated Jan. 17, 2013.
(Continued)

Primary Examiner — Patrick Hamo
(74) Attorney, Agent, or Firm — Marshall, Gerstein & Borun LLP (57) ABSTRACT A vacuum pump for generating an underpressure has a pump chamber (14, 15) with an inlet (143) and an outlet (150), wherein the outlet (150) is equipped with a valve (3). According to the invention, the pump chamber (14, 15) is provided with a pressure sensor (23, 23', 24). This vacuum pump has a relatively precise and inexpensive vacuum sensor. It is also advantageous that the sensor, being integrated in the pump chamber, is not susceptible to failure and takes up a small amount of space.

14 Claims, 7 Drawing Sheets (52) U.S. Cl.
CPC ....... *A61M 1/06* (2013.01); *A61M 2205/3306* (2013.01); *A61M 2205/3331* (2013.01)

(56) References Cited

U.S. PATENT DOCUMENTS

| | | |
|---|---|---|
| 2004/0265149 A1 | 12/2004 | Harigaya et al. |
| 2007/0060873 A1 | 3/2007 | Hiraoka et al. |
| 2007/0078383 A1 | 4/2007 | Tashiro et al. |
| 2008/0255503 A1 | 10/2008 | Quackenbush et al. |
| 2010/0179472 A1 | 7/2010 | Weston |
| 2011/0232388 A1* | 9/2011 | Butterfield ............. A61B 5/021 73/705 |

FOREIGN PATENT DOCUMENTS

| | | |
|---|---|---|
| WO | WO-2006/032156 A1 | 3/2006 |
| WO | WO-2008/057218 A2 | 5/2008 |
| WO | WO-2011/027117 A2 | 3/2011 |
| WO | WO-2011/035447 A1 | 3/2011 |

OTHER PUBLICATIONS

Written Opinion of the International Searching Authority for International Application No. PCT/CH2012/000222, dated Jan. 17, 2013.

\* cited by examiner

VACUUM PUMP

TECHNICAL FIELD

The present invention relates to a vacuum pump.

PRIOR ART

Vacuum pumps are used to generate underpressure. They can be used, for example, as breastpumps for expressing breastmilk and as drainage pumps, particularly in the field of thorax drainage or wound drainage. Diaphragm vacuum pumps can be relatively small and inexpensive.

WO 2011/035447 discloses a motor-driven breastpump for expressing breastmilk, with a vacuum diaphragm which, at the same time as generating or conveying the vacuum, is used for media separation between air and milk and serves as a transporting means for the expressed milk. The vacuum diaphragm is either driven directly by a motor and mechanical force-transmitting means or is connected to a vacuum-generating pump unit via a vacuum line.

WO 2008/057218 likewise discloses a vacuum diaphragm of a breastpump. This vacuum diaphragm is connected to a pump unit via a pressure line. It has an integrally formed valve flap.

Particularly in the case of drainage pumps, it is known to measure the generated vacuum or the vacuum applied to the user. Normally, the underpressure is measured by sensors of a known type inside the vacuum pump in a vacuum line or in an external suction or vacuum line. For example, piezoelectric sensors are used for this purpose. In the case of breastpumps, measurement of the generated underpressure has not been customary to date.

A great many pressure sensors are known in the prior art. Thus, US 2003/0116702 discloses an optical pressure sensor with a housing, a diaphragm held therein with a light blocker, a photodiode, a photodetector, and prisms which lead light from the photodiode to the photodetector. The position of the diaphragm, and therefore the position of the light blocker in the beam path between photodiode and photodetector, is dependent on the pressure in the housing.

WO 03/034014 discloses a pressure sensor for determining a fluid pressure, wherein the pressure is transmitted to a sensor via a diaphragm.

WO 2011/027117 also relates to a pressure sensor that uses a diaphragm to transmit the pressure.

DISCLOSURE OF THE INVENTION

It is an object of the invention to create an improved vacuum pump with a pressure sensor, which vacuum pump can be used in particular as a breastpump for expressing human breastmilk.

The vacuum pump according to the invention for generating an underpressure has a pump chamber with an inlet and an outlet, wherein the outlet is equipped with a valve. The outlet is preferably provided with the valve, in particular a non-return valve. According to the invention, the pump chamber is provided with a pressure sensor, respectively a pressure sensor is arranged in the pump chamber.

By arranging the pressure sensor on or in the vacuum chamber, here also called the pump chamber, it is possible for the vacuum pump to be made small and compact. No additional line to a pressure sensor is needed. By the arrangement of the sensor element on or in the vacuum chamber, the underpressure is measured in situ, and no losses and leakages have to be taken into account. The determination of the underpressure is therefore relatively precise.

The measured vacuum value can be used to control the pump, can be shown to the user on a pump display, or can be used in other ways.

The pressure sensor preferably comprises a sensor diaphragm, which is deflected according to the pressure prevailing in the pump chamber and thus transmits to a detector the prevailing pressure or the extent of a pressure change. The sensor diaphragm thus forms the sensor element.

In a preferred embodiment, a vane is arranged on the sensor diaphragm, and the position of the vane relative to the pump chamber is detectable. The vane and the rest of the sensor diaphragm are preferably formed together in one piece, the vane preferably being stiffer than the rest of the sensor diaphragm. The vane thus forms a transmission element which forwards the information regarding the deflection of the sensor diaphragm, i.e. the pressure change.

The deflection of the sensor diaphragm, in particular the position change of the protruding vane, can be detected by known means, for example by capacitive or inductive means. In a preferred embodiment, the position of the diaphragm is detected by an optical detection means.

The optical detection means preferably comprises a light emitter and a light detector, and the vane is movable, by deflection of the sensor diaphragm, into a light path between light emitter and light detector. The detected amount of light depends on how far the vane protrudes into the light path and, after suitable conversion, thus indicates the deflection of the sensor diaphragm and, consequently, the pressure prevailing in the pump chamber.

This sensor is preferably used in a diaphragm vacuum pump in which a vacuum diaphragm forms a wall of the pump chamber, wherein the volume of the pump chamber is reduced and increased by movement of the vacuum diaphragm and, consequently, the underpressure in the pump chamber is generated cyclically.

In a preferred embodiment, the vacuum diaphragm and the sensor diaphragm are formed together in one piece. Preferably, the sensor diaphragm in this case forms an extension of one side of the vacuum diaphragm. It is preferably arranged in an edge area of the vacuum diaphragm.

In another preferred embodiment, the vacuum diaphragm and the sensor diaphragm are two parts formed separately from each other. In this case, both are preferably round.

The sensor diaphragm and the vacuum diaphragm are preferably made of silicone or of a thermoplastic elastomer (TPE). The sensor diaphragm can be thinner or thicker than the vacuum diaphragm. It preferably has the same thickness, in particular 0.8 mm.

The vacuum diaphragm in particular is preferably plate-shaped with circular recesses and elevations.

In a preferred embodiment, the pump chamber has a first chamber area and a second chamber area, which is connected to this first chamber area via a through-opening. Both chamber areas have the same pressure level. The first chamber area serves as pump area, and the second one as sensor area. If diaphragms are used, the vacuum diaphragm preferably covers the first chamber area, and the sensor diaphragm covers the second chamber area. The inlet is preferably arranged in the first chamber area, and the outlet arranged in the second chamber area.

The through-opening is narrower than the first chamber area and is preferably composed of a connecting channel between the first chamber area and the second chamber area.

The second chamber area can have the same diameter as the connecting channel or can be made wider or provided with a greater volume. The volume of the connecting channel and/or the diameter of the through-opening also remains constant upon movement of sensor diaphragm and vacuum diaphragm. The volumes of the first and second chamber areas change as the diaphragms move. The first chamber area is preferably substantially larger than the second chamber area.

In a preferred embodiment, the vacuum diaphragm has a central point, and this central point is connectable to a drive element for the actuation of the vacuum diaphragm. A connection head for connection to the drive unit is preferably arranged at this central point.

The vacuum pump according to the invention can be used in particular as a breastpump for expressing breastmilk, or as a drainage pump, in particular for wound or thorax drainage. The vacuum diaphragm can be driven directly by a motor and a mechanical force-transmitting unit, for example a connecting rod. However, it can also be operated manually or can be connected via a vacuum line to a motorized or manually operated vacuum-generating pump unit.

In particular, the breastshield-side pump chamber of the media-separating diaphragm according to WO 2011/035447 can be equipped with a pressure sensor of this kind.

Further embodiments are set out in the dependent claims.

BRIEF DESCRIPTION OF THE DRAWINGS

Preferred embodiments of the invention are described below with reference to the drawings, which serve only for illustration and are not to be interpreted as limiting the invention. In the drawings.

DESCRIPTION OF PREFERRED EMBODIMENTS

Figure 1:
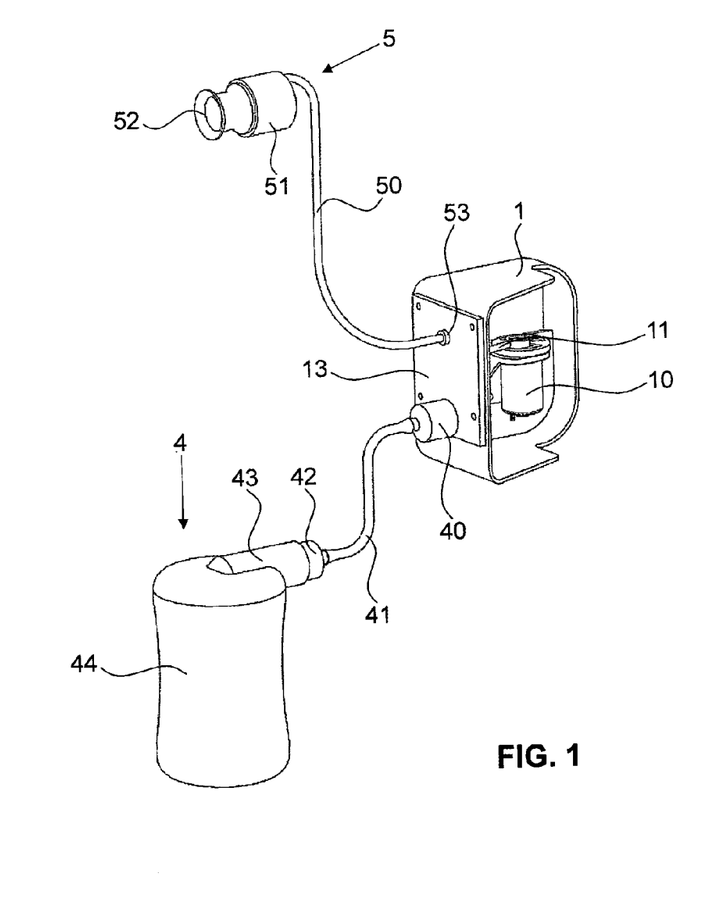
FIG. 1 shows a perspective view of a vacuum pump according to the invention in use as a breastpump.

FIG. 1 shows a first illustrative embodiment of the vacuum pump according to the invention in the form of a breastpump for expressing human breastmilk. It has a housing 1 of a vacuum pump with an electric motor 10. A breastshield unit 5 comprises a breastshield 51, with a breastshield funnel 52 that can be placed sealingly on a mother's breast, and a first line 50. This first line 50 can be connected releasably to the housing 1 of the vacuum pump via a first coupling part 53. A milk collection unit 4 has a milk collection container 44, with a connector stub 43, and also a second line 41. This second line 41 is provided with a second coupling part 40, with which it can be connected releasably to the housing 1 of the vacuum pump. At the opposite end of the second line 41 there is a third coupling part 42, which can be plugged into the connector stub 43 or pushed over the latter.

Figure 2:
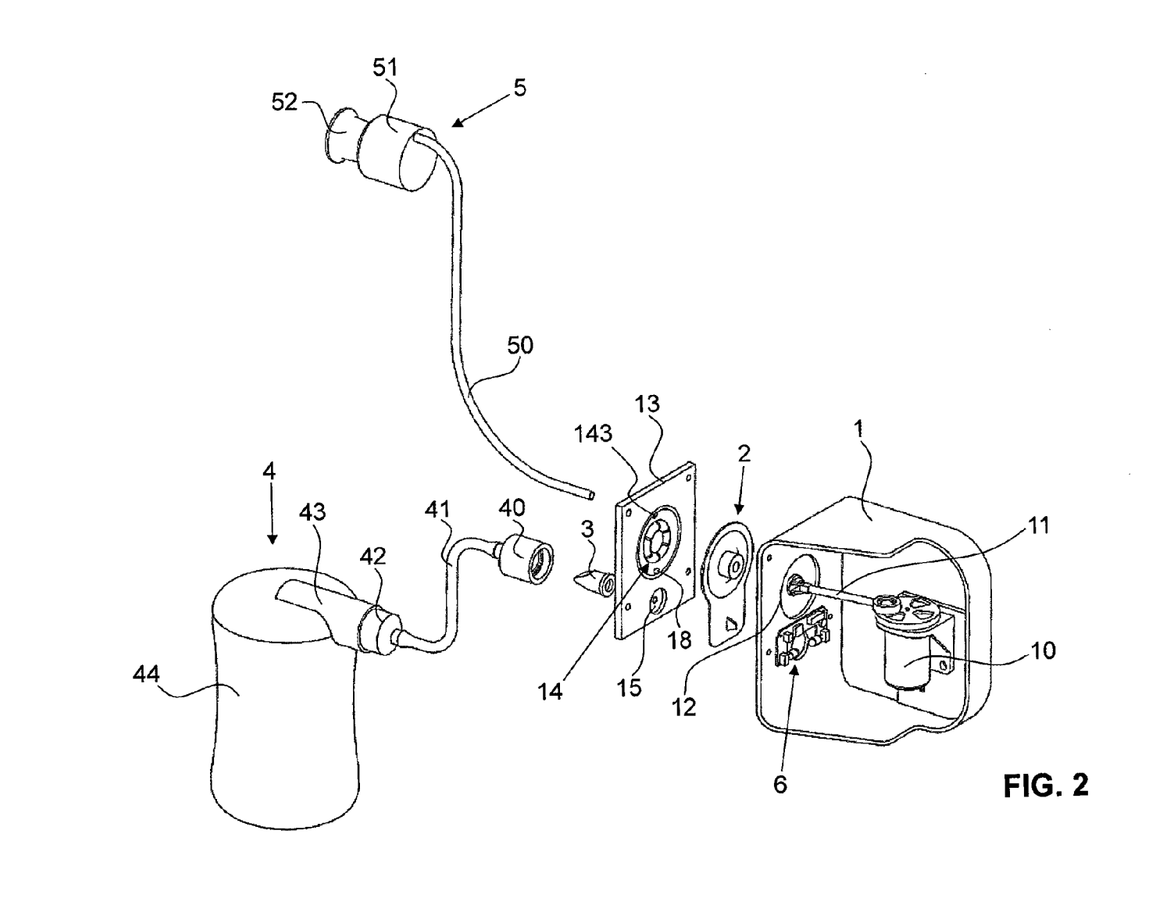
FIG. 2 shows the vacuum pump according to FIG. 1 in a partially exploded view.

As can be seen from FIG. 2, a cover 13 is fastened on an outer wall of the housing 1. It is preferably fastened releasably, for example screwed on. In this cover 13, a pump chamber is formed facing towards the housing 1. The pump chamber is composed of two chamber areas 14, 15. Both chamber areas 14, 15 are substantially circular and each form a recess in the cover 13. The first chamber area 14 has a substantially greater diameter than the second chamber area 15. The two chamber areas 14, 15 are connected to each other via a connecting channel 18. Except for its two openings leading into the chamber areas 14, 15, the connecting channel 18 is completely closed. It normally has no valves.

In the first chamber area 14, there is an inlet opening 143 to which the first coupling part 53 of the breastshield unit 5 can be connected. It is plugged in here. In the second chamber area 15, there is an outlet opening 150 which, against the outer face of the cover 13, is provided with a valve 3. This outlet opening 150 is preferably arranged centrally in the circular chamber area 15. The valve is preferably a non-return valve, in particular a spout valve. Other valve types can also be used.

The first chamber area 14 has a circular sealing edge 140. At a distance from this sealing edge 140, a closed ring 141 is present with an inner, preferably flat bottom surface 144. Radial grooves 142 pass through the ring and connect the bottom surface 144 to the outside of the ring 141. The inlet opening 143 and the near end of the connecting channel 18 are situated between sealing edge 140 and ring 141, and they preferably lie diametrically opposite each other. This can be seen clearly in FIG. 3.

In the intended use of the breastpump, the inlet opening 143 is preferably arranged above the connecting channel 18, or the first chamber area 14 above the second chamber area 15.

Figure 4:
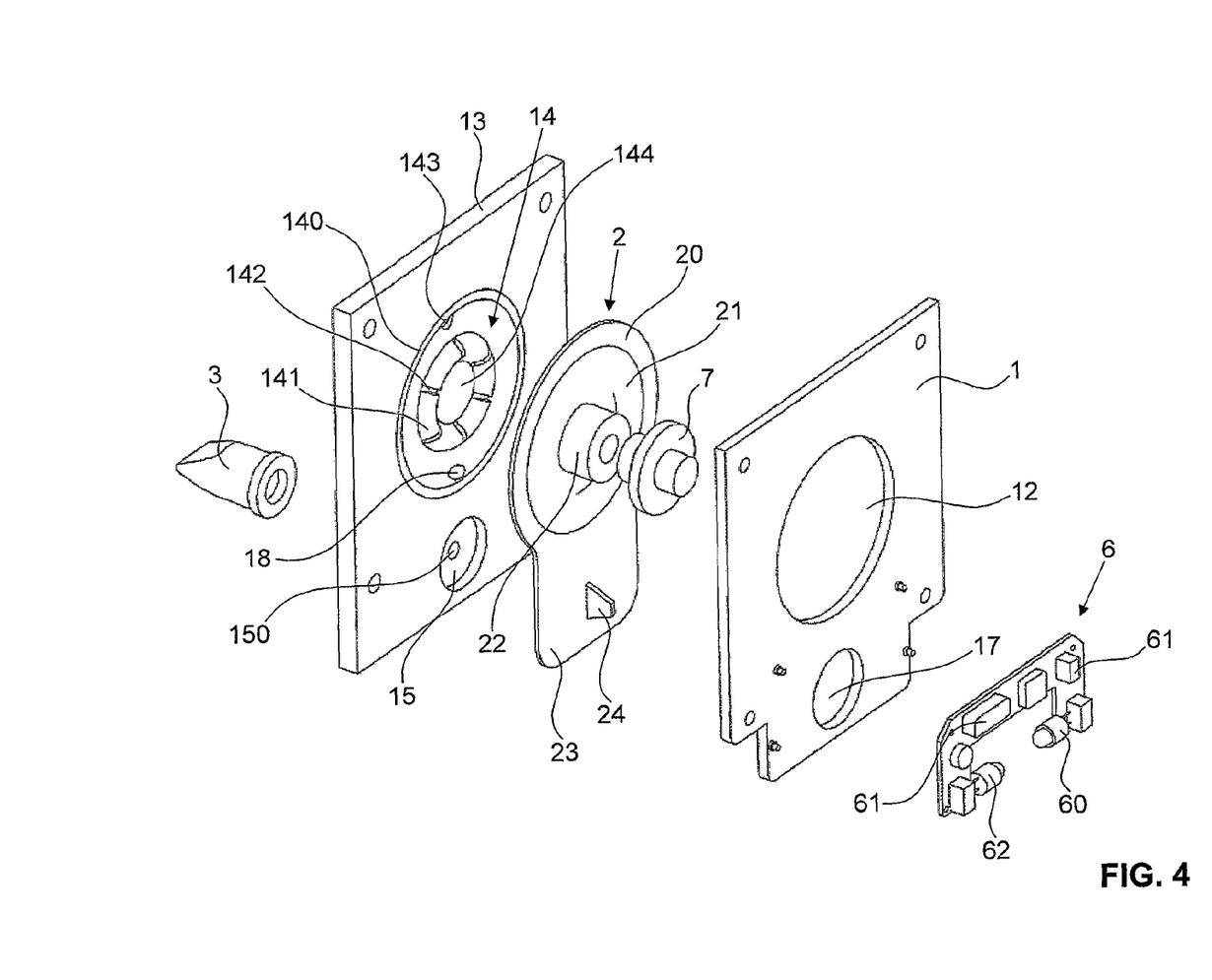
FIG. 4 shows part of the vacuum pump according to FIG. 2 in a further enlarged exploded view, with a sensor unit of a slightly different design.

A diaphragm 2 is arranged between cover 13 and the outer wall of the housing 1. This diaphragm 2 is preferably made of silicone or of a thermoplastic elastomer (TPE). The diaphragm 2 has a circular diaphragm body 21, with an edge 20 almost completely surrounding the latter. The diaphragm body 21 with its edge 20 is preferably plate-shaped. It preferably has elevations and depressions. A connection head 22 is integrally formed on the membrane body 21 at the centre thereof or is fastened thereto. This connection head 22 is connected releasably or non-releasably to a force-transmitting rod 11 of the drive via a coupling part 7 (see FIG. 4).

Figure 3:
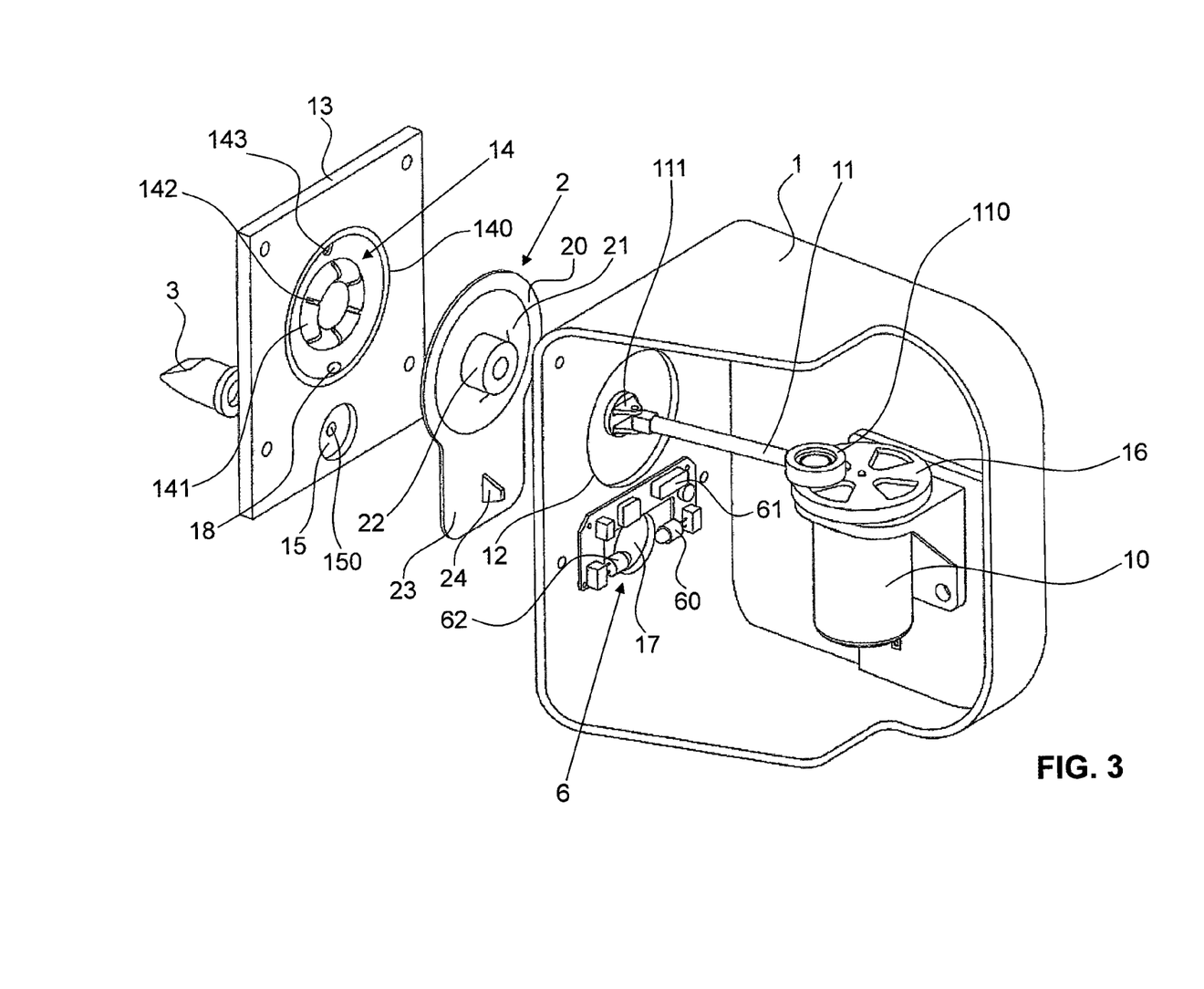
FIG. 3 shows an enlarged detail of the vacuum pump according to FIG. 2.

As can be clearly seen in FIG. 3, the drive comprises said electric motor 10, which is provided with a rotary disc 16. A connecting-rod head 110 of the force-transmitting rod 11, for example a connecting rod, is arranged on the rotary disc 16. An end of the force-transmitting rod 11 remote from the connecting-rod head 110 is designed as a connection element 111. This connection element 111 is connected to the diaphragm 2 via the coupling part 7. For this purpose, the housing 1 has a first through-opening 12. Thus, a rotation movement of the motor 10 is converted by the force-transmitting rod 11 into a linear movement of the diaphragm 2, more exactly of the diaphragm body 21.

The diaphragm body 21 covers the first chamber area 14, in particular the ring 141 and the cavity surrounded by the latter. By means of the linear movement of the diaphragm 2 along the longitudinal axis of the connection head 22, it is possible to generate an underpressure in the interior of the cavity and therefore in the first chamber area 14. Diaphragm body 21 and edge 20 thus form a vacuum diaphragm for generating an underpressure. The first chamber area 14 forms a pump area for generating the vacuum.

The diaphragm 2 also has an extension at one end in the form of a tab 23. The tab 23 here is substantially rectangular and flat. A lug or vane 24 is integrally formed on this tab 23 and protrudes perpendicularly from the tab 23 in the direction of the housing 1. The vane 24 is preferably stiffer than the tab 23 and than the rest of the diaphragm 20, 21. Only the connection head 22 preferably has an identical or greater stiffness.

The tab 23 covers the second chamber area 15, and the vane 24 preferably comes to lie over the outlet opening 150 in the assembled state. The vane 24 at least lies in the second chamber area 15. The area of the tab 23 is also held sealingly between the cover 13 and the outside of the housing wall 1, such that the pump chamber, formed by the two chamber areas 14 and 15, is sealed off from the housing 1. The outside of the housing wall 1 is preferably flat. The area of the tab 23 lying over the second chamber area 15 forms a sensor diaphragm. The second chamber area 15 forms a sensor area, as is explained below.

In the area of the vane 24, the housing 1 has a second through-opening 17, through which the vane 24 can extend. An optical sensor unit 6 is arranged on the inside of the housing 1, on both sides of this second through-opening 17. It has a light emitter 60, e.g. a photodiode, and a light detector 62, e.g. a photodiode. Light emitter 60 and light detector 62 are preferably arranged together with control and evaluation electronics 61 on a common printed circuit board. Light emitter 60 and light detector 62 are arranged lying diametrically opposite each other on the edge of the second through-opening 17. Light emitter 60 and light detector 62 define a light path or beam path, which extends perpendicularly with respect to the vane 24 and through which the latter can pass.

Figure 5:
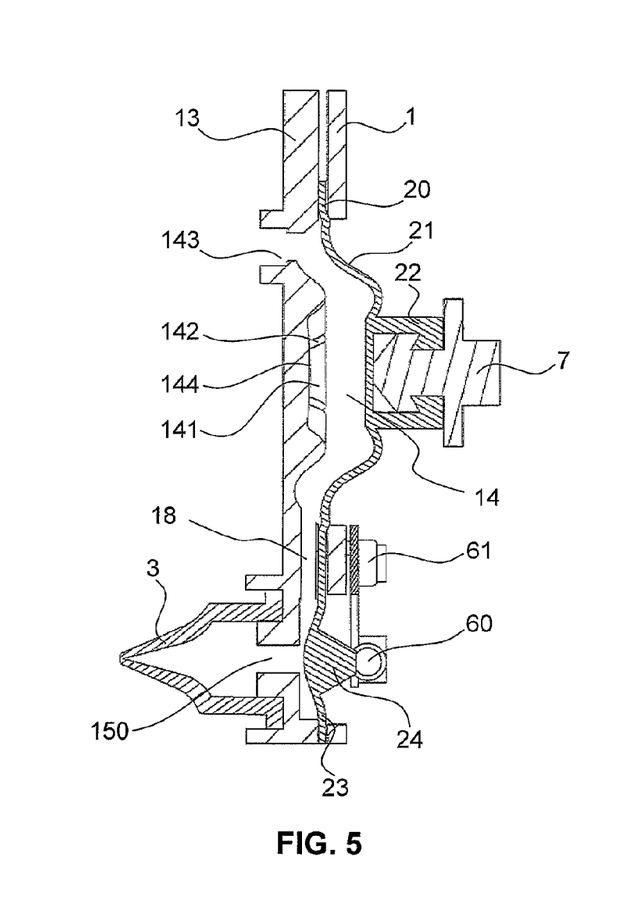
FIG. 5 shows a longitudinal section through the pump chamber of the vacuum pump according to FIG. 1, in a first position of the diaphragm.
Figure 6:
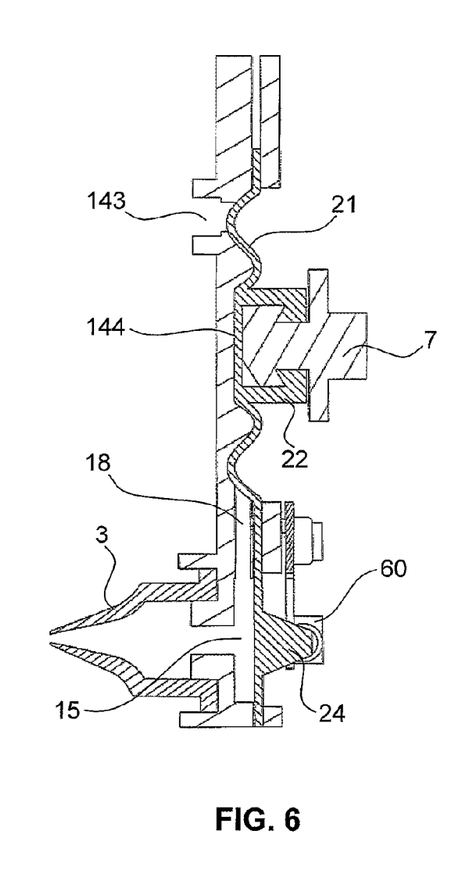
FIG. 6 shows a longitudinal section through the pump chamber of the vacuum pump according to FIG. 1, in a second position of the diaphragm.

The movement of the diaphragm 2 can now be seen in FIGS. 5 and 6. Both figures show how the edge 20 and the periphery of the tab 23 are clamped sealingly between the housing 1 and the cover 13.

In FIG. 5, the diaphragm 2, specifically the diaphragm body 21, is drawn towards the housing 1 via the coupling part 7 and the drive. The volume of the first chamber area 14 is increased. Air from the first line 50 of the breastshield unit 5 is sucked into the chamber. The non-return valve 3 is closed. By means of the underpressure arising in the first chamber area 14, the sensor diaphragm, that is to say the part of the tab 23 lying over the second chamber area 15, is also drawn into the second chamber area 15. In this way, the tab 23 moves towards the outlet opening 150 and therefore away from the light emitter 60 and light detector 62. The tab 23 thus moves at least partially out from the light path.

In FIG. 6, the diaphragm 2, again specifically the diaphragm body 21, is pressed towards the bottom surface 144. The diaphragm body 21 preferably lies on this bottom surface 144. The connection to the first line 50 of the breastshield unit 5 is preferably interrupted by the diaphragm 2 closing the inlet opening 143. The valve 3 is opened. The sensor diaphragm is relaxed and flat, and the vane 24 protrudes into the light path and thus at least partially covers the light emitter 60. This corresponds to a zero position for the measurement of the vacuum. Depending on the vacuum or underpressure generated, the sensor diaphragm with the vane 24, as can be seen in FIG. 5, is drawn to a differing extent out from the beam path, such that a defined amount of light can pass from the light emitter to the opposite light detector depending on the vacuum that is generated. This amount of light is defined by the control and evaluation electronics 61 and is assigned to a vacuum value. The measured vacuum value corresponds exactly to the vacuum value of the pump chamber, since the first chamber area 14 and the second chamber area 15 always lie at a common pressure level on account of the connecting channel 18. The position of the vane 24 in the light path can also be transmitted to a control unit of the pump, without assignment of a concrete vacuum value, and can be used to control the pump. Moreover, instead of an optical sensor unit 6, another means can also be used for detecting the position of the vane 24.

Figure 7:
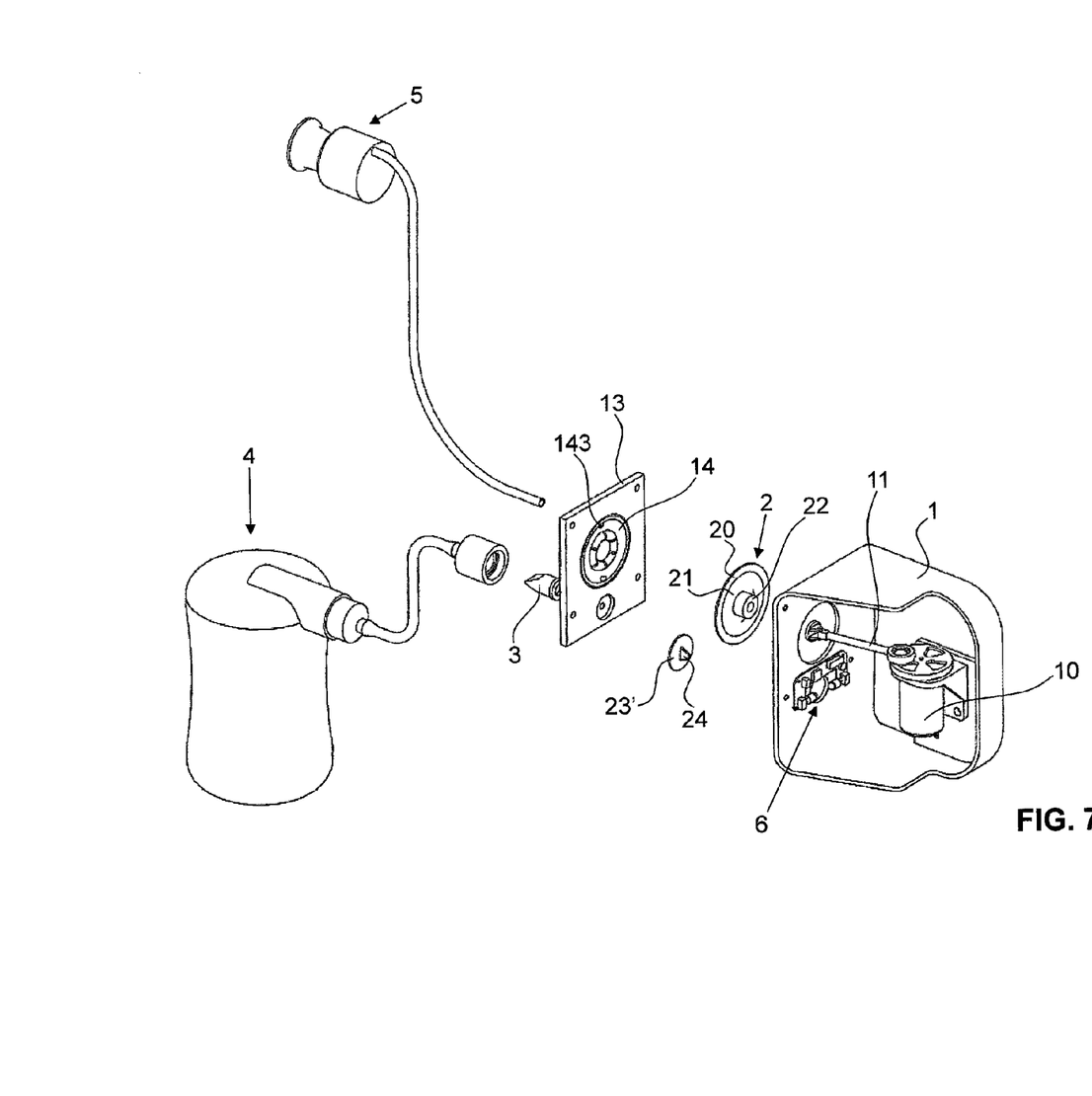
FIG. 7 shows a perspective exploded view of a vacuum pump according to the invention, in a second embodiment and in use as a breastpump.
Figure 8:
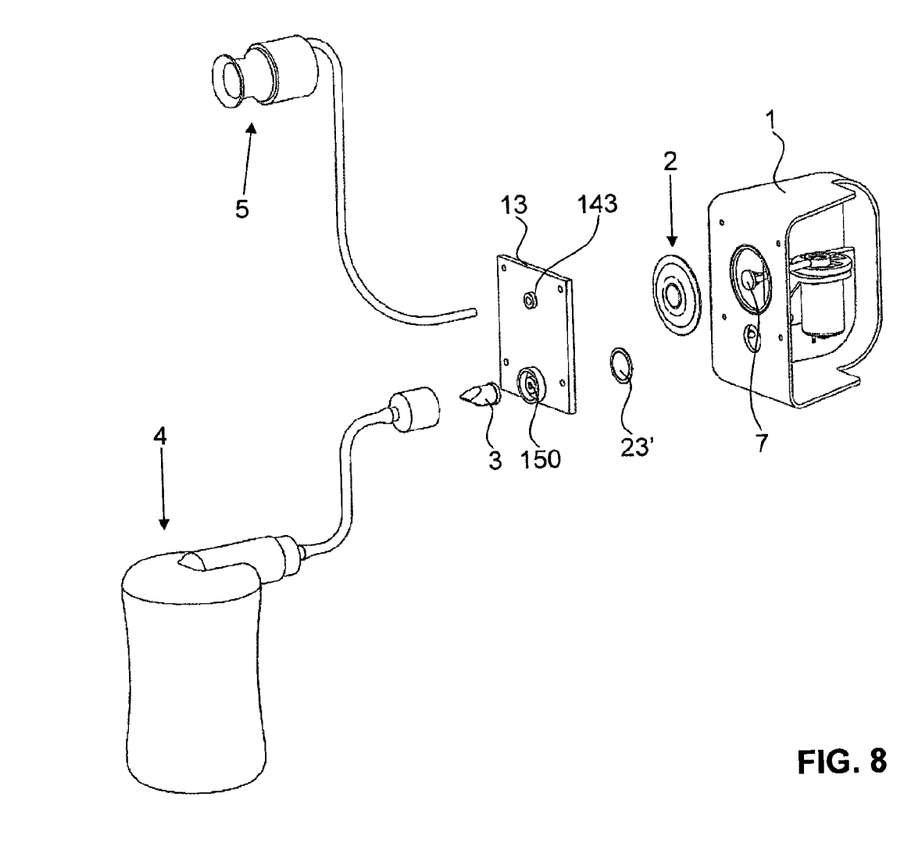
FIG. 8 shows a second perspective exploded view of the vacuum pump according to FIG. 7.

FIGS. 7 and 8 show a second illustrative embodiment. Here too, the vacuum pump according to the invention is used as a breastpump for expressing human breastmilk. Identical parts are designated by the same reference signs as in the first illustrative embodiment and are not described in any more detail here. However, in contrast to the first example, the diaphragm 2 is no longer shown in one piece. Vacuum diaphragm and sensor diaphragm are two diaphragms formed separately from each other. The vacuum diaphragm is round and is formed by the diaphragm body 21 and the edge 20. The sensor diaphragm 23' is likewise round here and is preferably flat and has the protruding vane 24. It can have a circumferential sealing edge.

As has already been described in WO 2011/035447, the expressed milk is pumped through the vacuum chamber or pump chamber in both of the abovementioned examples. The diaphragm 2 thus serves as a vacuum-generating diaphragm, for transporting the milk, and as media separation between the air in the housing of the pump and the milk. This diaphragm 2 can also be coupled to a vacuum-generating pump unit in accordance with the further illustrative embodiments of WO 2011/035447, such that it is moved by a cyclical underpressure that is applied to it via an underpressure line. In this case, it again generates an underpressure in the pump chamber 14, which underpressure is proportional to the applied cyclical underpressure of the vacuum unit. The other functions mentioned are thus maintained.

The vacuum pump according to the invention has a relatively precise and inexpensive vacuum sensor. It is also advantageous that the sensor, being integrated in the pump chamber, is not susceptible to failure and takes up a small amount of space.

The invention claimed is:

1. Vacuum pump for generating an underpressure, wherein the vacuum pump has a pump chamber with an inlet and an outlet wherein the outlet is equipped with a valve, wherein the pump chamber is provided with a pressure sensor, wherein the pump chamber has a first chamber area and a second chamber area, which is connected to this first chamber area via a through-opening, wherein the inlet is arranged in the first chamber area, and the outlet is arranged in the second chamber area, the pressure sensor comprising a sensor diaphragm, the vacuum pump having a vacuum diaphragm for generating the underpressure in the pump chamber, the vacuum diaphragm covering the first chamber area, and the sensor diaphragm covering the second chamber area.

2. Vacuum pump according to claim 1, wherein a vane is arranged on the sensor diaphragm, and the position of the vane relative to the pump chamber is detectable.

3. Vacuum pump according to claim 2, wherein an optical detection means is present in order to detect the position of the vane.

4. Vacuum pump according to claim 3, wherein the optical detection means comprises a light emitter and a light detector, and wherein the vane is movable, by deflection of the sensor diaphragm, into a light path between light emitter and light detector.

5. Vacuum pump according to claim 1, the vacuum pump having a vacuum diaphragm for generating the underpressure in the pump chamber, and the vacuum diaphragm and the sensor diaphragm are formed together in one piece.

6. Vacuum pump according to claim 5, wherein the sensor diaphragm is an extension of one side of the vacuum diaphragm.

7. Vacuum pump according to claim 1, the vacuum pump having a vacuum diaphragm for generating the underpressure in the pump chamber, and the vacuum diaphragm and the sensor diaphragm are two parts formed separately from each other.

8. Vacuum pump according to claim 1, wherein the vacuum diaphragm has substantially a round cross section.

9. Vacuum pump according to claim 8, wherein the vacuum diaphragm has a central point, and wherein this central point is connectable to a drive element for the actuation of the vacuum diaphragm.

10. Vacuum pump according to claim 9, wherein a connection head for connection to the drive element is arranged at the central point.

11. A vacuum pump unit for generating an underpressure, comprising:
 a vacuum pump;
 a pump chamber having an inlet and an outlet, the outlet being equipped with a valve;
 a pressure sensor including a sensor diaphragm having a vane arranged thereon;
 an optical detection means including a light emitter and a light detector, the vane being movable, by deflection of the sensor diaphragm, out of and into a light path between the light emitter and light detector, an amount of light passing from the light emitter to the light detector varying in relation to an extent to which the vane of the sensor diaphragm is moved out of the light path, which extent is determined by an amount of underpressure generated by the vacuum pump; and
 an evaluation electronics unit that assigns vacuum value based on the amount of light passing between the light emitter and the light detector, wherein the pump chamber includes a first chamber area and a second chamber area, the first and second chamber areas connected to one another via a connecting channel, whereby the first chamber area and the second chamber area always lie at a common pressure level, the sensor diaphragm covering an outlet of the second chamber area, the assigned vacuum valve corresponding to the underpressure in the pump chamber.

12. The vacuum pump unit of claim 11, the vacuum pump unit including a vacuum diaphragm for generating underpressure in the pump chamber.

13. The vacuum pump unit of claim 12, the vacuum diaphragm and the sensor diaphragm being formed together in one piece.

14. The vacuum pump unit of claim 12, the vacuum diaphragm and the sensor diaphragm being two parts formed separately from each other.

* * * * *